(12) United States Patent
Stuehle et al.

(10) Patent No.: US 10,085,625 B2
(45) Date of Patent: Oct. 2, 2018

(54) VIDEO CAMERA HOUSING FOR AN ENDOSCOPE

(71) Applicant: OLYMPUS WINTER & IBE GMBH, Hamburg (DE)

(72) Inventors: Sebastian Stuehle, Hamburg (DE); Patrick Scherr, Alt-Moelln (DE); Sebastian Jungbauer, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 148 days.

(21) Appl. No.: 14/425,955

(22) PCT Filed: Jul. 17, 2013

(86) PCT No.: PCT/EP2013/002119
§ 371 (c)(1),
(2) Date: Mar. 4, 2015

(87) PCT Pub. No.: WO2014/037067
PCT Pub. Date: Mar. 13, 2014

(65) Prior Publication Data
US 2015/0216399 A1    Aug. 6, 2015

(30) Foreign Application Priority Data

Sep. 5, 2012  (DE) .................. 10 2012 017 498

(51) Int. Cl.
*A61B 1/05*  (2006.01)
*A61B 1/04*  (2006.01)
(Continued)

(52) U.S. Cl.
CPC .............. *A61B 1/05* (2013.01); *A61B 1/0011* (2013.01); *A61B 1/00124* (2013.01);
(Continued)

(58) Field of Classification Search
CPC ............ A61B 1/00009; A61B 1/00105; A61B 1/00096; A61B 1/00163; A61B 1/0008;
(Continued)

(56) References Cited

U.S. PATENT DOCUMENTS 4,219,013 A     8/1980  Okada
4,784,118 A  *  11/1988  Fantone ................. A61B 1/002
                                                   359/434
(Continued)

FOREIGN PATENT DOCUMENTS

| | | |
|---|---|---|
| EP | 0496142 A1 | 7/1992 |
| JP | H05-057549 A | 1/1993 |
| JP | 2002301016 A * | 10/2002 |

OTHER PUBLICATIONS

English Translation of Aono (JP 2002301016A).*
(Continued)

*Primary Examiner* — John P Leubecker
*Assistant Examiner* — Pamela F Wu
(74) *Attorney, Agent, or Firm* — Scully, Scott, Murphy & Presser, P.C.

(57) ABSTRACT

A housing for accommodating optical and electronic components of a video camera of a medical video endoscope. The housing including: a first housing part, a second housing part, the housing parts assembled together to form inner chambers for mounting the optical and electronic components and an axial passage for optically connecting the inner chambers; a window disposed in an end opening in the assembled housing parts, electrical connectors disposed in a wall in the assembled housing parts, wherein, in an unassembled configuration, the inner chambers are accessible from a surface substantially transversely to a longitudinal axis of the housing parts, and the first and second housing parts are configured to mate with each other in such a way (Continued)

that the inner chambers are hermetically sealed from an exterior of the assembled first and second housing parts.

3 Claims, 2 Drawing Sheets

(51) Int. Cl.
*A61B 1/00* (2006.01)
*H04N 5/225* (2006.01)

(52) U.S. Cl.
CPC .......... *A61B 1/00126* (2013.01); *A61B 1/051* (2013.01); *H04N 5/2252* (2013.01); *H04N 5/2253* (2013.01); *A61B 2560/0406* (2013.01); *H04N 2005/2255* (2013.01)

(58) Field of Classification Search
CPC ............ A61B 1/00186; A61B 1/00188; A61B 1/0019; A61B 1/00193; A61B 1/0125; A61B 1/045; A61B 1/05; A61B 1/06; A61B 1/0607; A61B 1/00101; A61B 1/051; A61B 1/053; A61B 1/055; A61B 1/041
USPC ......................................................... 600/133
See application file for complete search history.

(56) References Cited

U.S. PATENT DOCUMENTS

| 4,794,911 | A |   | 1/1989 | Okada |
| 6,007,484 | A | * | 12/1999 | Thompson ......... A61B 1/00096 600/122 |
| 2002/0161284 | A1 | * | 10/2002 | Tanaka ............... A61B 1/00096 600/176 |
| 2006/0069312 | A1 |   | 3/2006 | O'Connor |
| 2008/0081947 | A1 |   | 4/2008 | Irion et al. |
| 2008/0204863 | A1 |   | 8/2008 | Vogeli |
| 2010/0261961 | A1 |   | 10/2010 | Scott et al. |
| 2011/0288372 | A1 |   | 11/2011 | Petersen |

OTHER PUBLICATIONS

International Preliminary Report on Patentability together with the Written Opinion dated Mar. 10, 2015 received in related International Application No. PCT/EP2013/002119.

International Search Report dated Sep. 25, 2013 issued in PCT/EP2013/002119.

* cited by examiner

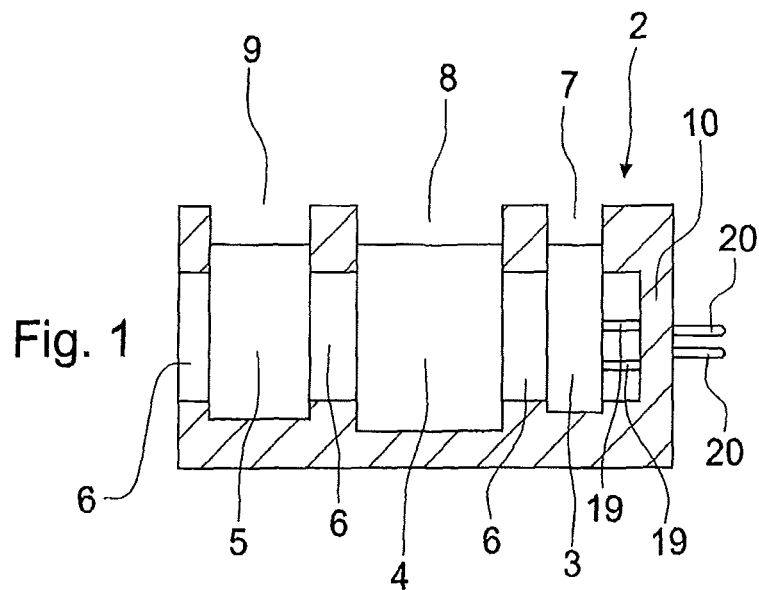
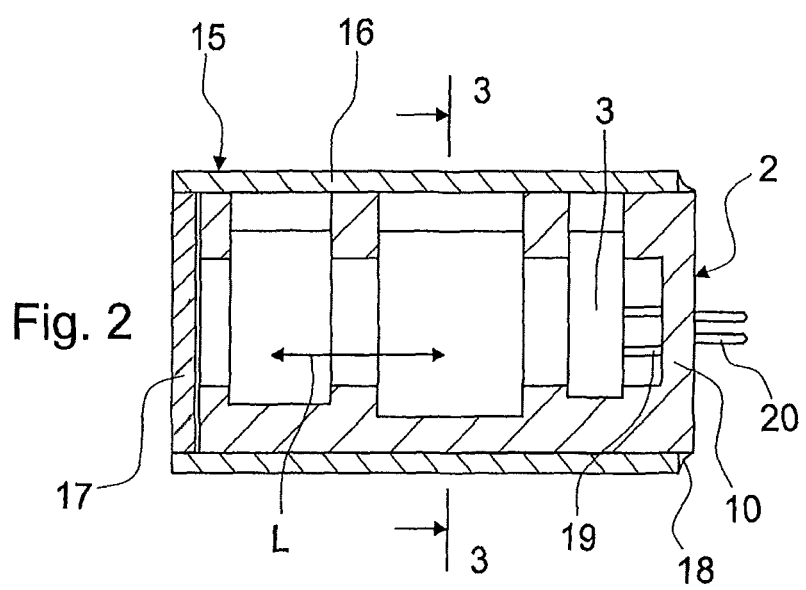

VIDEO CAMERA HOUSING FOR AN ENDOSCOPE

CROSS-REFERENCE TO RELATED APPLICATION

The present application is based upon and claims the benefit of priority from PCT/EP2013/002119 filed on Jul. 17, 2013, which claims benefit to DE 10 2012 017 498.5 filed on Sep. 5, 2012, the entire contents of each of which are incorporated herein by reference.

BACKGROUND

Field

The present invention generally relates to endoscopes, and to a housing of the type referred to in claim 1.

Prior Art

Video camera housings for a video endoscope in a single-piece embodiment are known from DE 10 2006 015 176 B3 and DE 199 55 229 C1. In this case, the housing consists substantially of a metal tube, in which the components to be introduced must be inserted and aligned from the end surfaces. This leads to complicated and expensive manufacturing steps.

DE 10 2004 023 866 B3 shows a generic housing which consists of two housing parts. These are designed as tube pieces pushed concentrically one above the other. The components may be distributed over the two tube pieces so that the installation position is slightly improved. Here again, however, access is also only possible by the end surfaces. The construction with the two tubes one inside the other is used by means of rotatable mounting of the two tubes against each other to create a rotation possibility for the video camera. The question of the hermetic sealing of the housing required remains open.

The non-generic state of the art according to DE 10 2008 056 830 A1 shows a housing having a longitudinally slotted and elastically resilient tube to hold the relay lenses of an endoscope optics system, which is surrounded by heat shrinkable tubing. In the case of heat shrinkable tubing that has not yet been mounted, it can be introduced and aligned very easily through the longitudinal slot from the side along its entire length.

SUMMARY

An object of the present invention is to enable the production of a generic housing.

According to the invention one of the housing parts has a laterally accessible access opening, which allows the insertion and alignment of components substantially more easily. This access opening is, however, only accessible in the unconnected state of the housing parts. If they are connected, then it is covered and closed by the hermetic connection of the housing parts. This embodiment allows assembly of the components even in the generic design of the housing with rigid housing parts, which are important for the precision mounting of the components of a video camera. The rigid design of the housing also allows for the simple manufacture by means of plastic injection molding process or ceramic sintering process, which are not possible with elastic or extendable housing embodiments. The invention can thus significantly reduce the manufacturing problems of the state of the art.

It is advantageous if the lateral surfaces, which the access opening has, are designed as a cylindrical outer surface of one housing part, wherein the other housing part forms a tube wall, which covers the cylindrical outer surface upon connection of the housing parts. In this case, one housing part is designed with the tube wall structurally very easily and can preferably be designed according to claim 3 together with the end wall bearing the window.

The proximal end wall with the electrical feed-throughs is advantageously arranged on the other housing part, which is enclosed by the tube wall. In an alternative embodiment the lateral surface is formed substantially planar, and not cylindrical as in the first embodiment. The lateral surface can be formed as a simple separating surface, which in the longitudinal direction divides the housing into two parts.

BRIEF DESCRIPTION OF THE DRAWINGS

In the drawings the invention is illustrated schematically and by way of example.

FIG. 1 shows a longitudinal section through a housing part of a housing according to the invention in a first embodiment, FIG. 2 shows the complete housing in sectional view according to FIG. 1.

DETAILED DESCRIPTION

Figure 3:
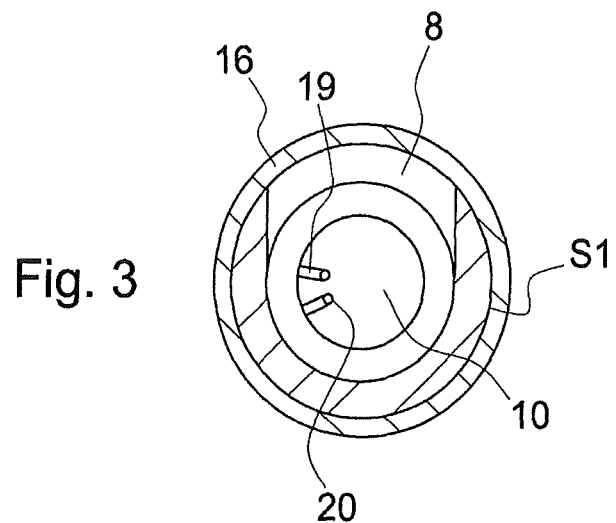
FIG. 3 shows a section according to line 3-3 in FIG. 2

FIGS. 1-3 show a housing 1 consisting of two housing parts 2 and 15 in a first embodiment. In FIG. 1 the inner housing part 2 is shown. FIGS. 2 and 3 show the complete housing 1, wherein the housing parts 2 and 15 are interconnected.

The inner housing part 2 is, as shown in FIG. 3, designed concentrically to a center axis and has three chambers 3, 4 and 5, which are connected to an axial passage opening 6. According to FIGS. 1 and 3, the chambers 3, 4 and 5 with access openings 7, 8 and 9 are accessible from the side. The inner housing part 2, with a proximal end wall 10, is closed on the end located at the right in FIG. 1.

Figure 4:
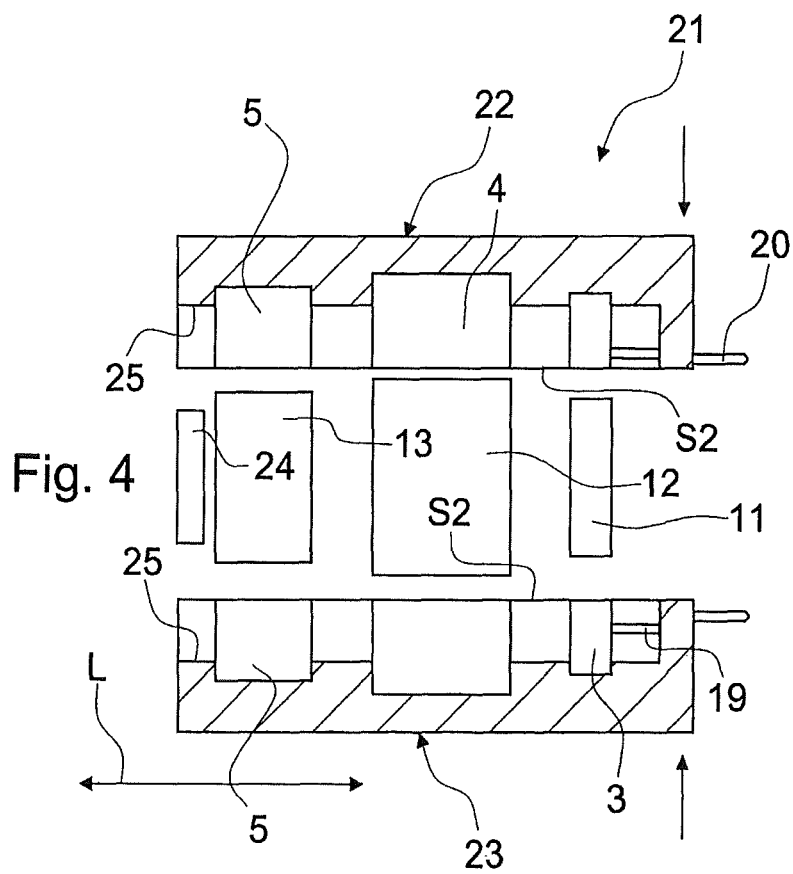
FIG. 4 shows in the longitudinal section according to FIG. 1 both housing parts of a housing in a second embodiment.

The chambers 3, 4 and 5 are, as a comparison of the figures shows, adapted to accommodate the components 11, 12 and 13 illustrated in FIG. 4, which can be inserted laterally through the access openings 7, 8 and 9 and are able to be accommodated securely in the chambers 3, 4 and 5.

The elements 11, 12 and 13 to be accommodated include electronic and optical components of a video camera. In the embodiment these are an electronic image sensor 11 and two optical components 12 and 13. In another embodiment only one optical component can also be provided in one chamber.

FIGS. 2 and 3 show the complete housing 1 with the inner housing part 2 illustrated in FIG. 1, but supplemented by the outer housing part 15. This consists of a tube wall 16, which supports the distal end wall, which is designed as a window 17 in the embodiment.

FIG. 3 shows that the inner housing part 2 has a cylindrical outer surface and that the tube wall 16 has an inner surface fitting to the cylindrical outer surface of the inner housing part 2, so that it closes, sealing the cylindrical outer surface of the inner housing part 2.

The construction illustrated is formed such that it is very easily hermetically sealed. The housing pails 2 and 15 can be manufactured in an injection molding technique out of plastic material adapted for these purposes or, for example, from ceramic material in the sintering process. Such materials are rigid and of sufficient strength to be able to mount with sufficient precision the components 11, 12 and 13 to be stored. They are also non-conductive and can ensure the necessary electrical insulation. Such materials are therefore advantageously suitable for supporting required electrical conductors or, optionally, being coated directly with electrical strip conductors.

The window 17 can be connected such that it is hermetically sealed to the tube wall 16, for example by soldering, for example after metallization of the surface regions to be connected. Finally, the housing parts 2 and 15 must still be hermetically connected. For this purpose a ring soldering 18 is provided in FIG. 2, which again may also require a prior metallization of the surface regions to be soldered.

The electronic image sensor 11 arranged in the chamber 3 must be joined via electrical conductors to the outside of the housing 1. This is illustrated in FIGS. 1 to 3. Electrical strip conductors 19 are visible in FIGS. 1 and 2, which are arranged on the inner wall of the inner housing part 2 and whose sections continuing on to the end wall 10 are illustrated in FIG. 3. The strip conductors 19 run to the end wall 10 until the inner ends of the contact pins 20, which pass through the end wall 10 and which are internally electrically contacted with the strip conductors 19 and are able to be contacted externally, for example, by a plug coupling, with which a continuing cable can be connected.

The strip conductors 19 are contacted suitably with the electronic image sensor 11. The details are not illustrated in the figures. The contact can be made via soldered joints, contact springs or the like.

The structural design of the inner housing part 2 with the access openings 7, 8 and 9 not only allows the convenient lateral loading insertion of the components 11, 12 and 13, but also the access to these in order to align them, for example, after insertion. Other work is also simplified after the insertion by the access openings, such as the soldering of the strip conductors 19.

The access opening 7 can also assist in attaching the strip conductors 19 conveniently. If the inner housing 2 is designed as a molded interconnected device, the strip conductors 19 can be manufactured, for example, by laser direct structuring. The access for the laser can then be provided simply by the access opening 7.

In the embodiment of FIGS. 1 to 3 the housing parts 2 and 15 are interconnected on a cylindrical surface or the housing 1 is divided into these two housing parts by means of a cylindrical surface.

A second embodiment of the invention is illustrated in FIG. 4. This shows a housing 21 with two housing parts 22 and 23. Further details of FIG. 4, which correspond to the embodiment of FIGS. 1 to 3, are indicated by the same reference numerals.

If the housing parts 22 and 23 are pushed together in the direction of the two arrows in FIG. 4, then they meet in a surface which forms the separating surface of the housing 21 and lies in the longitudinally extending center plane. The assembled housing 21 corresponds substantially to the assembled housing 1, which is illustrated in FIG. 2. The difference is the position of the separating surface.

In the embodiment of FIG. 2 the separating surface between the two housing parts 2 and 15 is the cylindrical outer surface of inner housing part 2, which forms a circumferential cylindrical lateral surface S1 (FIG. 3). In FIG. 4 the separating surface is not cylindrical, but a planar surface, which forms the central separating surface of the housing 21 and also in each case forms a lateral surface S2 of each of the two housing parts 22 and 23 relative to the longitudinal direction of the housing. The longitudinal direction of the housing is illustrated in FIGS. 2 and 4 with the double arrow L. It is clear that the surface vertical of the planar separating surface S2 of the embodiment of FIG. 4 is perpendicular to the longitudinal direction. This also applies to all of the surface verticals of the cylindrical separating surface S1 of the embodiment of FIG. 2.

In FIG. 4, in turn, the components 11, 12 and 13 are illustrated as fitting the housing parts 22 and 23. When closing the housing parts in the direction of the two arrows in FIG. 4 the components are accommodated in the chambers. In the embodiment of FIG. 4 a window 24 is also illustrated that, when closing the housing parts, is enclosed by an annular wall 25 and able to be soldered in this. A seal around the edge of the separating surface is still required for the hermetic sealing of the housing 21. Here, a circumferential soldering or suitable bonding is again possible.

The electrical connection of the image sensor 11 can also take place in the embodiment of FIG. 4 corresponding to that of FIGS. 1 to 3, as shown in FIG. 4.

Thus, FIG. 4 shows that the chambers 3, 4 and 5 each have a half in the housing part 22 and the other half in the housing part 23. The entire interior of the housing parts 22 and 23 is accessible from the central separating surface with a large access opening.

There are other, non-illustrated ways possibilities of separating the housing according to the invention into two housing parts. In the embodiment of FIG. 4, for example, the separating surface between the housing parts may be arranged off-center or even skewed.

Embodiments are also possible in which the housing is divided into more than two parts. In the embodiment of FIGS. 1 to 3, for example, one of the housing parts 2 or 15 can be subdivided in the longitudinal direction. The other housing part, continuing through, can therefore ensure continuous strength.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A housing for accommodating optical and electronic components of a video camera of a medical video endoscope, the housing comprising:
   a first housing part,
   a second housing part, the first and second housing parts assembled together to form inner chambers for mounting the optical and electronic components and axial passages for connecting the inner chambers;
   a window disposed in a distal end opening in the assembled first and second housing parts,
   one or more electrical feedthroughs disposed to be hermetically sealed in a proximal end wall in the assembled first and second housing parts, and
   an imaging sensor disposed within one of the inner chambers, the imaging sensor being electrically connected to the one or more electrical feedthroughs;
   wherein, prior to assembly and after disassembly of the first and second housing parts, the inner chambers are accessible from a direction substantially transverse to a longitudinal axis of the first and second housing parts and, after assembly of the first and second housing parts, the first and second housing parts are configured to mate together with each other in such a way that the inner chambers are hermetically sealed from an exterior of the assembled first and second housing parts; and the second housing part is a cylindrical tube and, in an assembled state, the first housing part is disposed within the cylindrical tube.

2. The housing according to claim 1, wherein the distal end opening is arranged on a distal end side of the second housing pall.

3. The housing according to claim 1, wherein the proximal end wall is arranged on a proximal end side of the first housing part.

\* \* \* \* \*